(12) United States Patent
Mou et al.

(10) Patent No.: US 11,543,397 B2
(45) Date of Patent: Jan. 3, 2023

(54) AIR DETECTION SYSTEM

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW); Yi-Ting Lu, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 124 days.

(21) Appl. No.: 17/146,615

(22) Filed: Jan. 12, 2021

(65) Prior Publication Data
US 2021/0223222 A1    Jul. 22, 2021

(30) Foreign Application Priority Data
Jan. 16, 2020 (TW) .................................. 109101600

(51) Int. Cl.
  *G01N 33/00* (2006.01)
  *G01N 1/22* (2006.01)
  *G01N 15/06* (2006.01)
(52) U.S. Cl.
  CPC ....... *G01N 33/0073* (2013.01); *G01N 1/2273* (2013.01); *G01N 15/06* (2013.01); *G01N 2015/0693* (2013.01)

(58) Field of Classification Search
  CPC .. G01N 33/0073; G01N 1/2273; G01N 15/06; G01N 2015/0693; G01N 2015/0046; G01N 15/0205
  See application file for complete search history.

(56) References Cited

FOREIGN PATENT DOCUMENTS

| CN | 2932374 Y | * | 8/2007 |
| CN | 204836339 U | | 12/2015 |
| CN | 209432182 U | | 9/2019 |
| JP | 2013-127681 A | | 6/2013 |
| TW | M581748 U | | 8/2019 |
| WO | WO-2018076405 A1 | * | 5/2018 |

* cited by examiner

*Primary Examiner* — David Z Huang
(74) *Attorney, Agent, or Firm* — Birch, Stewart, Kolasch & Birch, LLP

(57) ABSTRACT

An air detection system is provided and includes an intelligent device and an internet of things processing device. The intelligent device includes an inlet, an outlet, a gas-flowing channel, a control module and a gas detection module. The gas-flowing channel is disposed between the inlet and the outlet. The control module is disposed in the intelligent device and includes a processor and a transmission unit. The gas detection module is disposed in the gas-flowing channel and electrically connected to the control module. The gas detection module includes a piezoelectric actuator and at least one sensor. The piezoelectric actuator inhales gas into the gas-flowing channel through the inlet and discharges the gas through the outlet. The sensor detects the introduced gas to obtain gas information and transmits the gas information to the control module. The internet of things processing device is connected to the transmission unit of the intelligent device for receiving the gas information.

11 Claims, 18 Drawing Sheets

AIR DETECTION SYSTEM

FIELD OF THE INVENTION

The present disclosure relates to an air detection system, and more particularly to an air detection system, which combines an intelligent device with a gas detection module and connects the intelligent device to an internet of things processing device.

BACKGROUND OF THE INVENTION

Recently, people pay more and more attention to the air pollution. In order to confirm the quality of the air, it is feasible to use a gas sensor to detect the air surrounding in the environment. If the detection information can be provided in real time to warn the people in the environment, it would be helpful for avoiding the harm and facilitating people to be away from the hazard immediately. Thus, it prevents the hazardous gas exposed in the environment from affecting the human health and causing the harm. Therefore, using a gas sensor to detect the air in the surrounding environment is a very good application.

Therefore, how to combine an intelligent device with a gas detection module and connect the intelligent device to an internet of things processing device for allowing the user to not only confirm body information in real time but also monitor the air quality in real time is the main subject in the present disclosure.

SUMMARY OF THE INVENTION

An object of the present disclosure is to provide an air detection system utilizing a gas detection module combined with the intelligent device to obtain an air quality information in the surrounding environment around the user in anytime, so that the user can acknowledge the air condition of the surrounding environment in real time.

In accordance with an aspect of the present disclosure, an air detection system including at least one intelligent device and an internet of things processing device is provided. The intelligent device includes at least one inlet, at least one outlet, a gas-flowing channel, a control module and a gas detection module. The gas-flowing channel is disposed between the at least one inlet and the at least one outlet. The control module is disposed in the intelligent device and includes a processor and a transmission unit. The gas detection module is disposed in the gas-flowing channel and electrically connected to the control module. The gas detection module includes a piezoelectric actuator and at least one sensor. The piezoelectric actuator inhales gas outside the intelligent device into the gas-flowing channel through the at least one inlet and discharges the gas out of the intelligent device through the at least one outlet. The at least one sensor detects the gas introduced to obtain gas information and transmits the gas information to the control module. The internet of things processing device is connected to the transmission unit of the intelligent device for receiving the gas information transmitted from the intelligent device.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of the preferred embodiments of this invention are presented herein for purpose of illustration and description only. It is not intended to be exhaustive or to be limited to the precise form disclosed.

Figure 1:
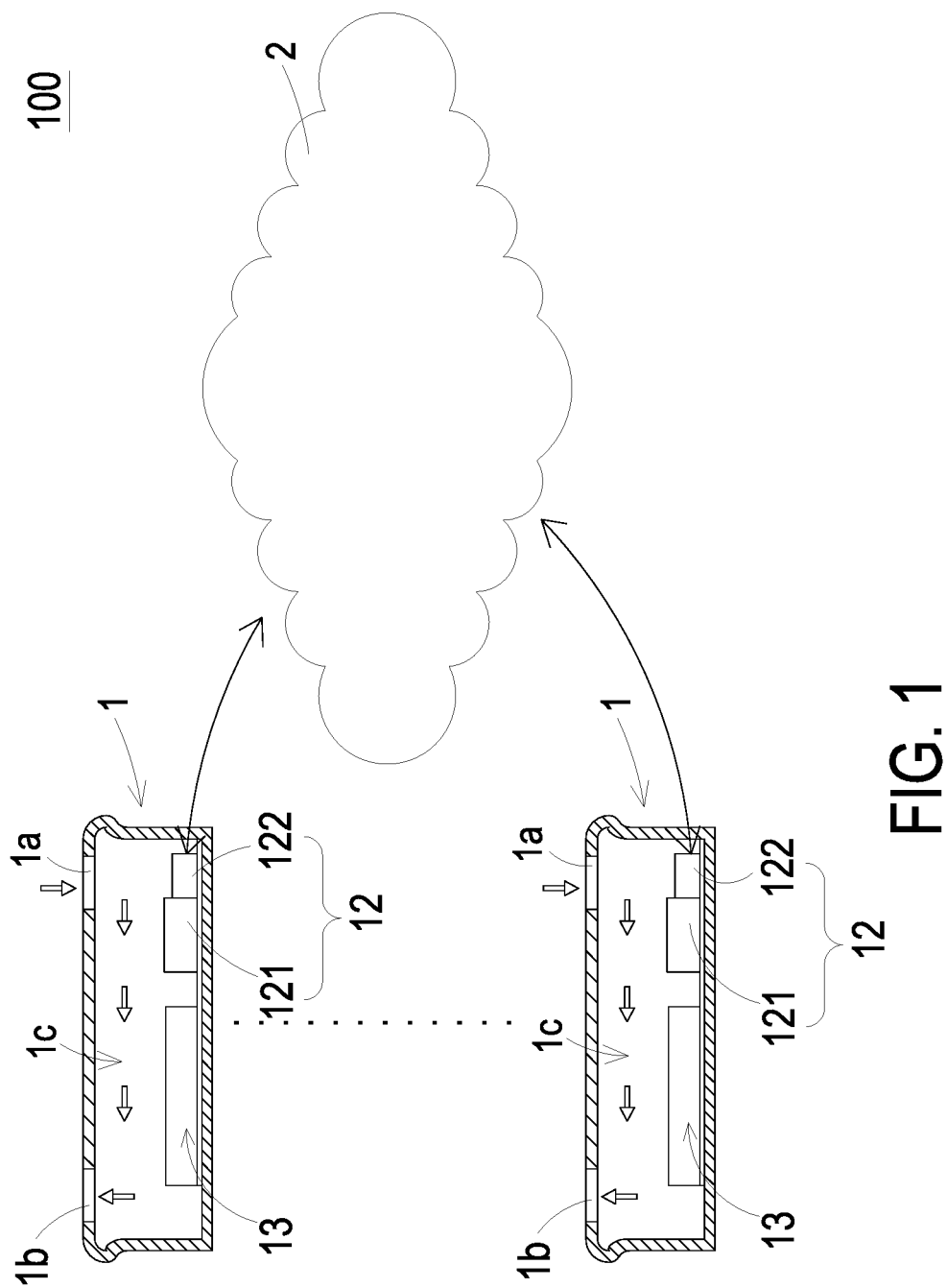
FIG. 1 is a schematic view illustrating an air detection system according to an embodiment of the present disclosure.

Please refer to FIG. 1. The present disclosure provides an air detection system 100 including an intelligent device 1 and an internet of things processing device 2. The intelligent device 1 is one selected from the group consisting of an intelligent city, an intelligent building, an intelligent factory, a public air quality detector, an intelligent street lamp, a security surveillance camera, and a HVAC (heating, ventilation and air conditioner) and a combination thereof.

The intelligent device 1 includes at least one inlet 1a, at least one outlet 1b, a gas-flowing channel 1c, a control module 12 and a gas detection module 13. In the embodiment, the numbers of the at least one inlet 1a and the at least one outlet 1b are respectively illustrated with one, but not limited thereto. The gas-flowing channel 1c is disposed between the inlet 1a and the outlet 1b. The gas detection module 13 is disposed in the gas-flowing channel 1c and detects the gas in the gas-flowing channel 1c to obtain a gas information. The control module 12 is disposed in the intelligent device 1 and electrically connected to the gas detection module 13. The control module 12 includes a processor 121 and a transmission unit 122. The processor 121 transmits a driving signal to the gas detection module 13 to control the activation and operation of the gas detection module 13, calculate the gas information detected by the gas detection module 13, and transmit the calculated gas information to the internet of things processing device 2 through the transmission unit 122 for storing and analyzing.

Please refer to FIGS. 2A to 2C, 3A, 3B, 4, 5A and 5B. In the embodiment, the gas detection module 13 includes a base 131, a piezoelectric actuator 132, a driving circuit board 133, a laser component 134, a particulate sensor 135 and an outer cover 136. The base 131 includes a first surface 1311, a second surface 1312, a laser loading region 1313, a gas-inlet groove 1314, a gas-guiding-component loading region 1315 and a gas-outlet groove 1316. In the embodiment, the first surface 1311 and the second surface 1312 are two surfaces opposite to each other. In the embodiment, the laser loading region 1313 is hollowed out from the first surface 1311 to the second surface 1312. The gas-inlet groove 1314 is recessed from the second surface 1312 and disposed adjacent to the laser loading region 1313. The gas-inlet groove 1314 includes a gas-inlet 1314a and two lateral walls. The gas-inlet 1314a is in communication with an environment outside the base 131, and spatially corresponds to an inlet opening 1361a of the outer cover 136. A transparent window 1314b is opened on the two lateral walls and is in communication with the laser loading region 1313. Therefore, the first surface 1311 of the base 131 is covered and attached by the outer cover 136, and the second surface 1312 is covered and attached by the driving circuit board 133. Thus, the gas-inlet groove 1314 and the driving circuit board 133 define an inlet path.

In the embodiment, the gas-guiding-component loading region 1315 is recessed from the second surface 1312 and is in fluid communication with the gas-inlet groove 1314. A ventilation hole 1315a penetrates a bottom surface of the gas-guiding-component loading region 1315. In the embodiment, the gas-outlet groove 1316 includes a gas-outlet 1316a, and the gas-outlet 1316a spatially corresponds to the outlet opening 1361b of the outer cover 136. The gas-outlet groove 1316 includes a first section 1316b and a second section 1316c. The first section 1316b is hollowed out from the first surface 1311 in a vertical projection area of the gas-guiding-component loading region 1315 spatially corresponding thereto. The second section 1316c is hollowed out from the first surface 1311 to the second surface 1312 in a region where the first surface 1311 is not aligned with the vertical projection area of the gas-guiding-component loading region 1315 and extended therefrom. The first section 1316b and the second section 1316c are connected to form a stepped structure. Moreover, the first section 1316b of the gas-outlet groove 1316 is in communication with the ventilation hole 1315a of the gas-guiding-component loading region 1315, and the second section 1316c of the gas-outlet groove 1316 is in fluid communication with the gas-outlet 1316a. Therefore, when the first surface 1311 of the base 131 is attached and covered by the outer cover 136, and the second surface 1312 of the base 131 is attached and covered by the driving circuit board 133, the gas-outlet groove 1316, the outer cover 136 and the driving circuit board 133 would define an outlet path altogether.

Figure 2A:
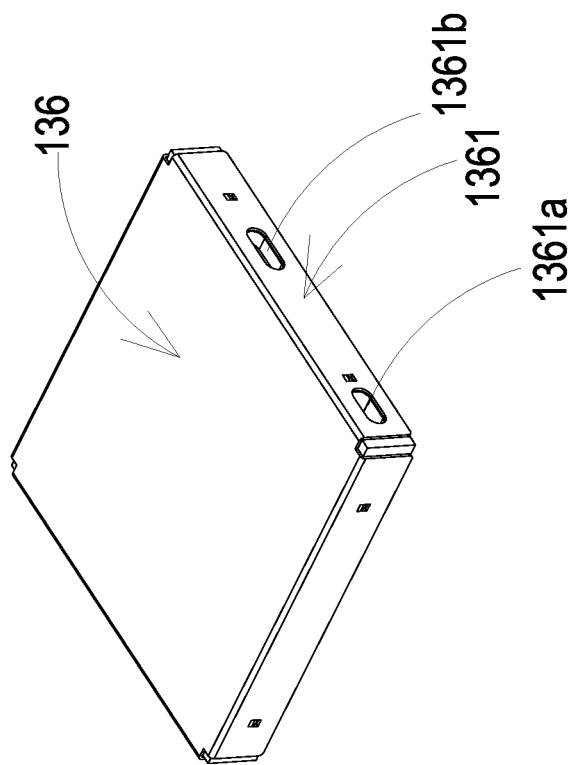
FIG. 2A is schematic exterior view illustrating a gas detection module according to an embodiment of the present disclosure.
Figure 2B:
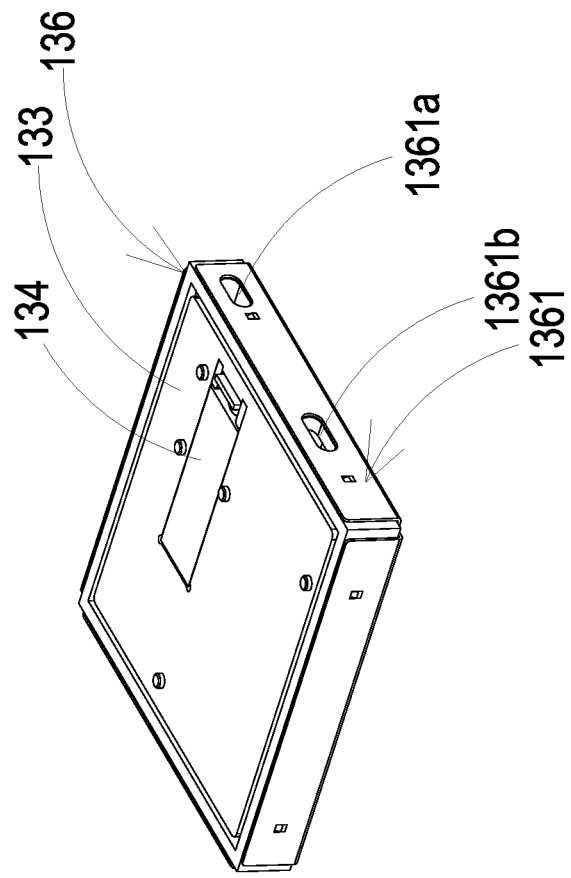
FIG. 2B is a schematic exterior view illustrating the gas detection module according to the embodiment of the present disclosure and taken from another perspective angle.
Figure 2C:
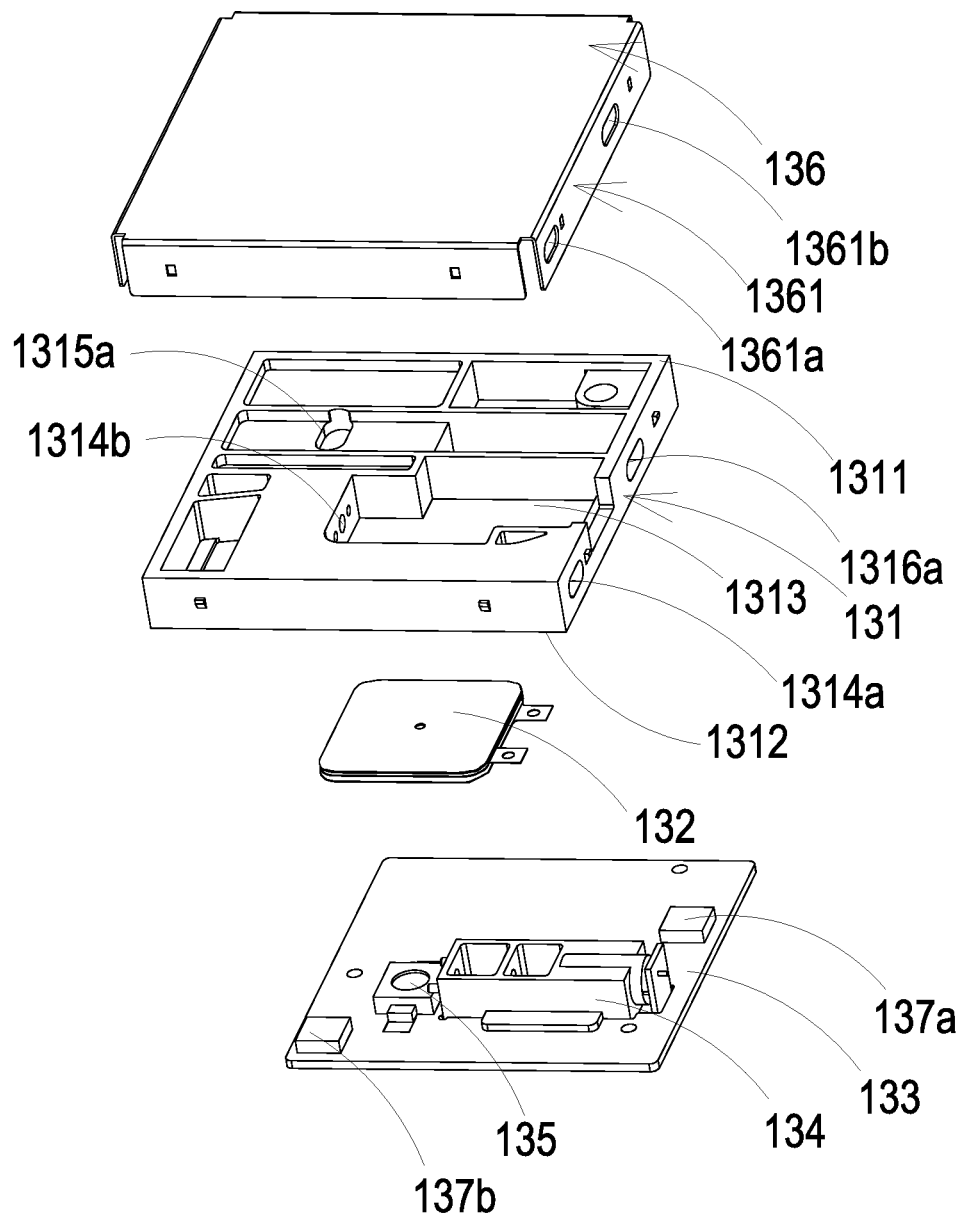
FIG. 2C is a schematic exploded view illustrating the gas detection module of the present disclosure.
Figure 3A:
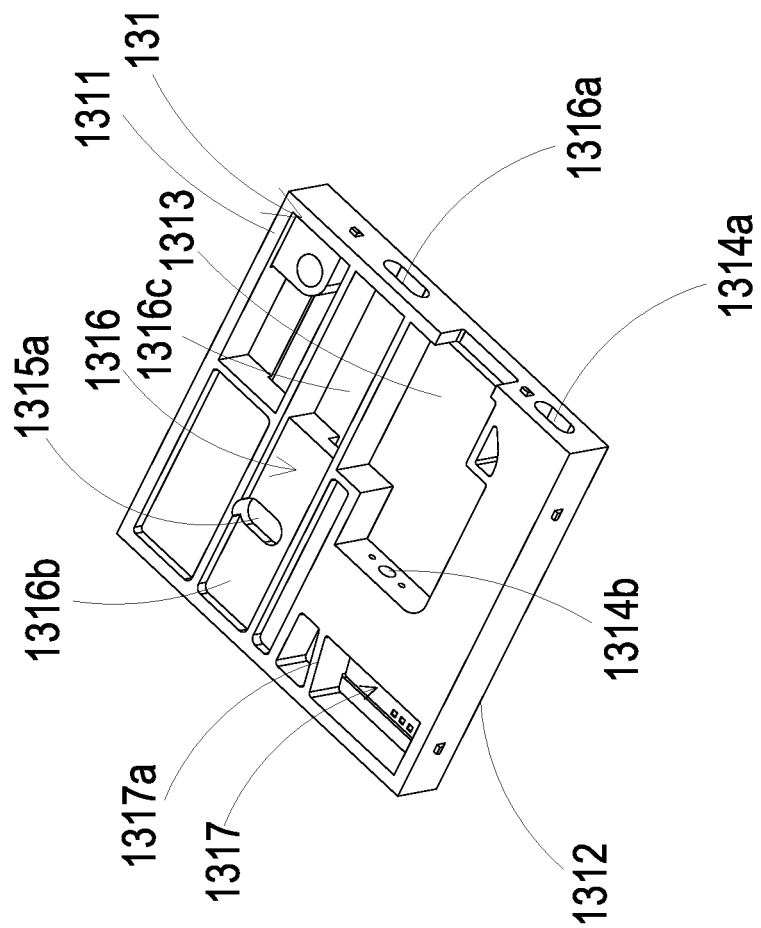
FIG. 3A is a schematic perspective view illustrating a base of the gas detection module of the present disclosure.
Figure 3B:
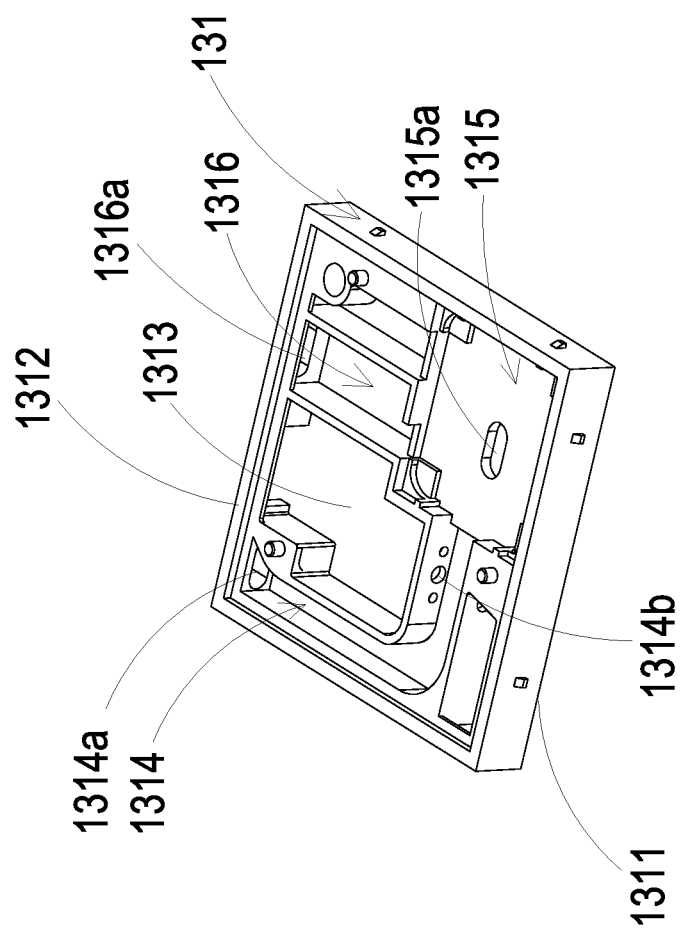
FIG. 3B is a schematic perspective view illustrating the base of the gas detection module of the present disclosure and taken from another perspective angle.
Figure 4:
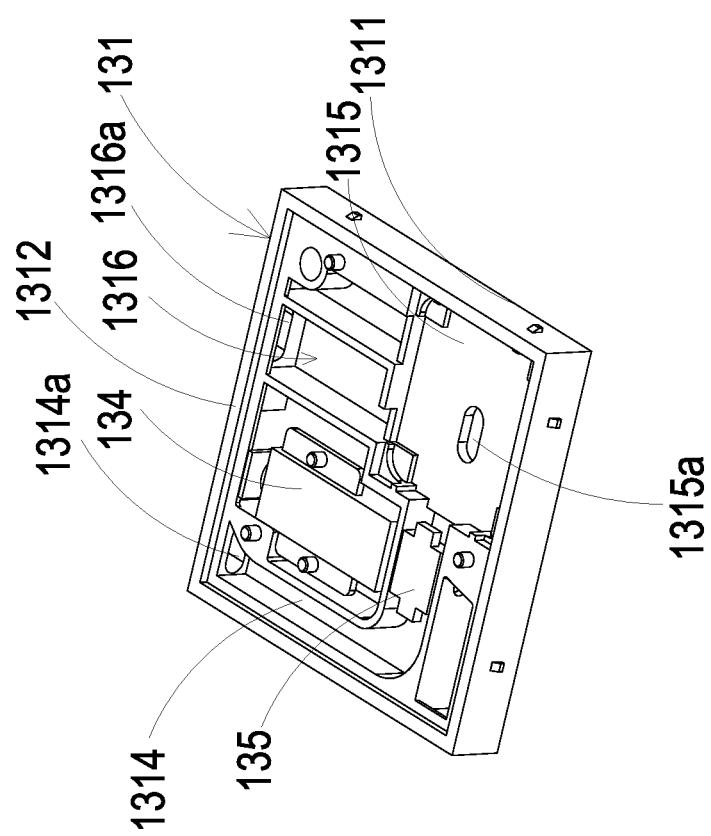
FIG. 4 is a schematic perspective view illustrating a laser component and a particulate sensor accommodated in the base of the present disclosure.

Please refer to FIG. 2C and FIG. 4. In the embodiment, the laser component 134 and the particulate sensor 135 are disposed on the driving circuit board 133 and accommodated in the base 131. In order to describe the positions of the laser component 134 and the particulate sensor 135 in the base 131, the driving circuit board 133 is omitted specially in FIG. 4 for the purpose of clarity. Please refer to FIG. 2C, FIG. 3B, FIG. 4 and FIG. 9. In the embodiment, the laser component 134 is accommodated in the laser loading region 1313 of the base 131, and the particulate sensor 135 is accommodated in the gas-inlet groove 1314 of the base 131 and aligned to the laser component 134. In addition, the laser component 134 spatially corresponds to the transparent window 1314b, a light beam emitted from the laser component 134 passes through the transparent window 1314b and is irradiated into the gas-inlet groove 1314. A light beam path emitted from the laser component 134 passes through the transparent window 1314b and extends in a direction perpendicular to the gas-inlet groove 1314, thereby forming an orthogonal direction with the gas-inlet groove 1314.

In the embodiment, a projecting light beam emitted from the laser component 134 passes through the transparent window 1314b and enters the gas-inlet groove 1314, irradiates the suspended particles contained in the gas passing through the gas-inlet groove 1314, and generates scattered light spots. The scattered light spots are received and calculated by the particulate sensor 135 for obtaining related information in regards to the sizes and the concentration of the suspended particles contained in the gas. In the embodiment, the particulate sensor 135 is a PM2.5 sensor.

Figure 5A:
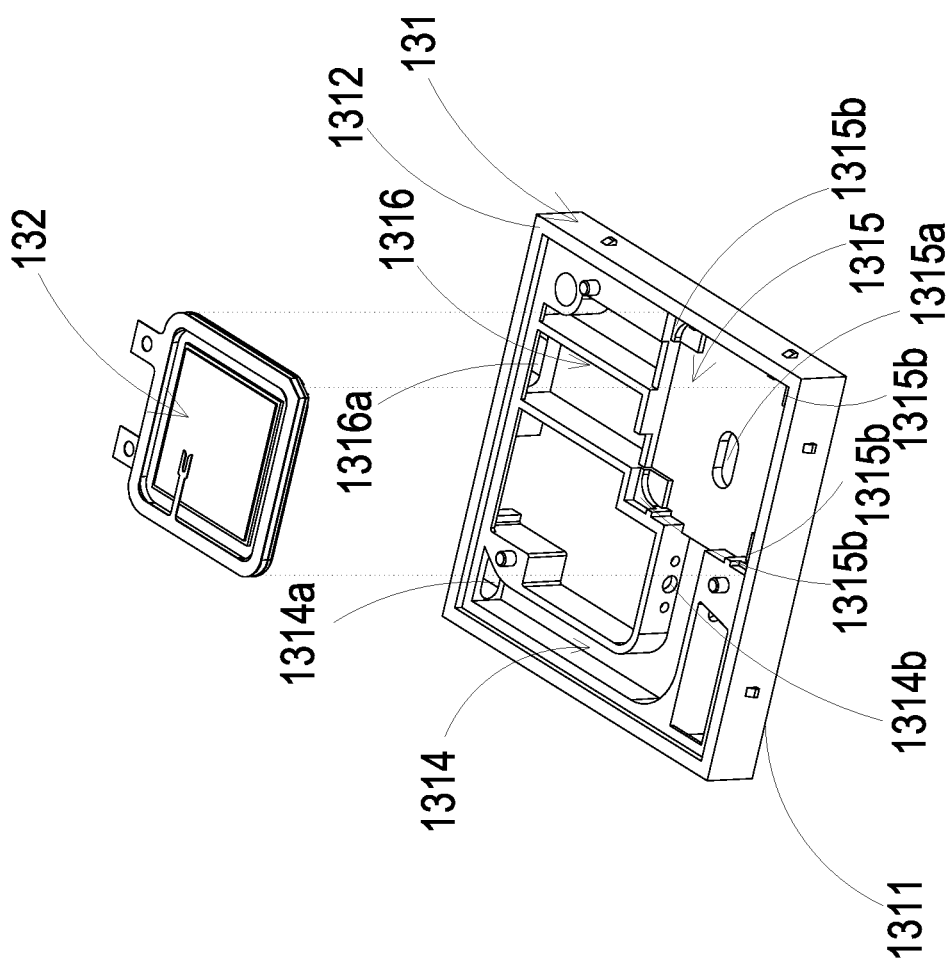
FIG. 5A is a schematic exploded view illustrating the combination of the piezoelectric actuator and the base according to the present disclosure.
Figure 5B:
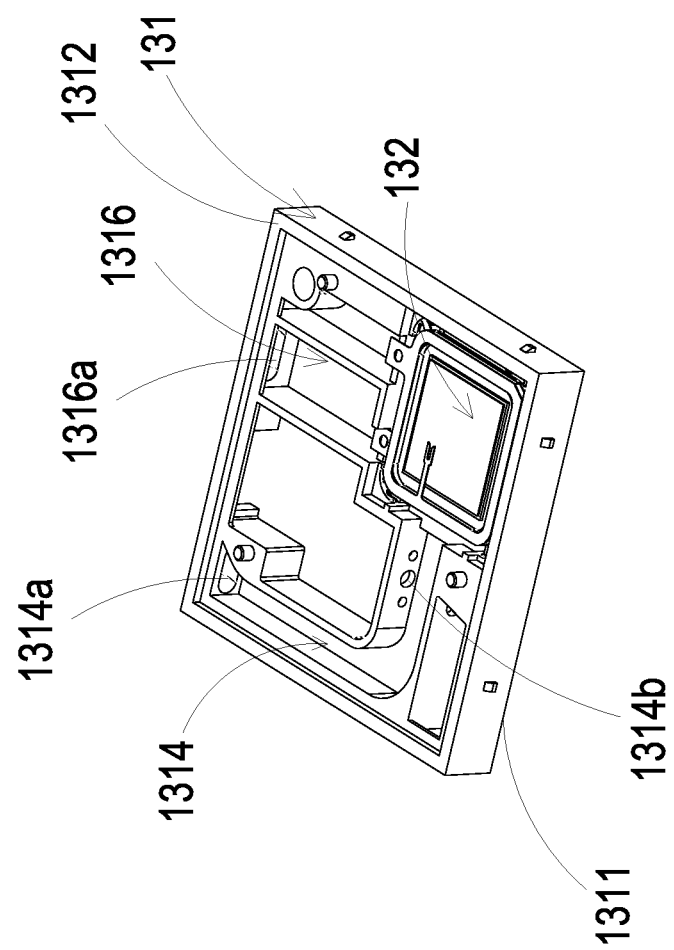
FIG. 5B is a schematic perspective view illustrating the combination of the piezoelectric actuator and the base according to the present disclosure.

Please refer to FIG. 5A and FIG. 5B. The piezoelectric actuator 132 is accommodated in the gas-guiding-component loading region 1315 of the base 131. Preferably but not exclusively, the gas-guiding-component loading region 1315 is square and includes four positioning protrusions 1345b disposed at four corners of the gas-guiding-component loading region 1315, respectively. The piezoelectric actuator 132 is disposed in the gas-guiding-component loading region 1315 through the four positioning protrusions 1315b. In addition, as shown in FIGS. 3A, 3B, 8B and 8C, the gas-guiding-component loading region 1315 is in communication with the gas-inlet groove 1314. When the piezoelectric actuator 132 is enabled, the gas in the gas-inlet groove 1314 is inhaled by the piezoelectric actuator 132, so that the gas flows into the piezoelectric actuator 132. Furthermore, the gas is transported into the gas-outlet groove 1316 through the ventilation hole 1315a of the gas-guiding-component loading region 1315. Moreover, through the operation of the piezoelectric actuator 132, the gas outside the intelligent device 1 is inhaled through the at least one inlet 1a, transported and passed by the gas detection module 13, and is discharged out through the at least one outlet 1b. The particulate sensor 135 detects the gas introduced to obtain the gas information.

Figure 8A:
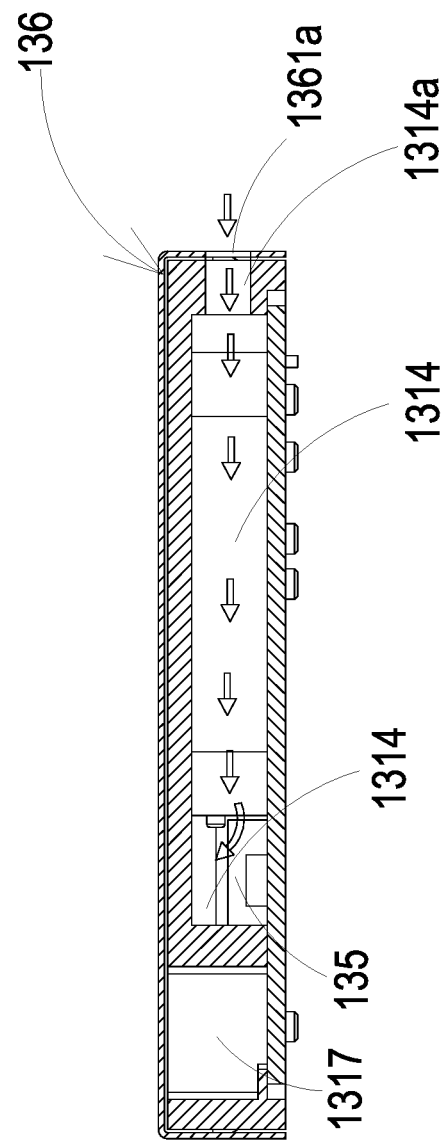
FIGS. 8A to 8C schematically illustrate gas flowing paths of the gas detection module of the present disclosure.

Please refer to FIGS. 2A to 2C. In the embodiment, the driving circuit board 133 covers and is attached to the second surface 1312 of the base 131, and the laser component 134 is positioned and disposed on the driving circuit board 133, and is electrically connected to the driving circuit board 133. The particulate sensor 135 is positioned and disposed on the driving circuit board 133, and is electrically connected to the driving circuit board 133. The outer cover 136 covers the base 131 and is attached to the first surface 1311 of the base 131. Moreover, the outer cover 136 includes a side plate 1361. The side plate 1361 has an inlet opening 1361a and an outlet opening 1361b. When the outer cover 136 covers the base 131, the inlet opening 1361a spatially corresponds to the gas-inlet 1314a of the base 131 (as shown in FIG. 8A), and the outlet opening 1361b spatially corresponds to the gas-outlet 1316a of the base 131 (as shown in FIG. 8C).

Figure 6A:
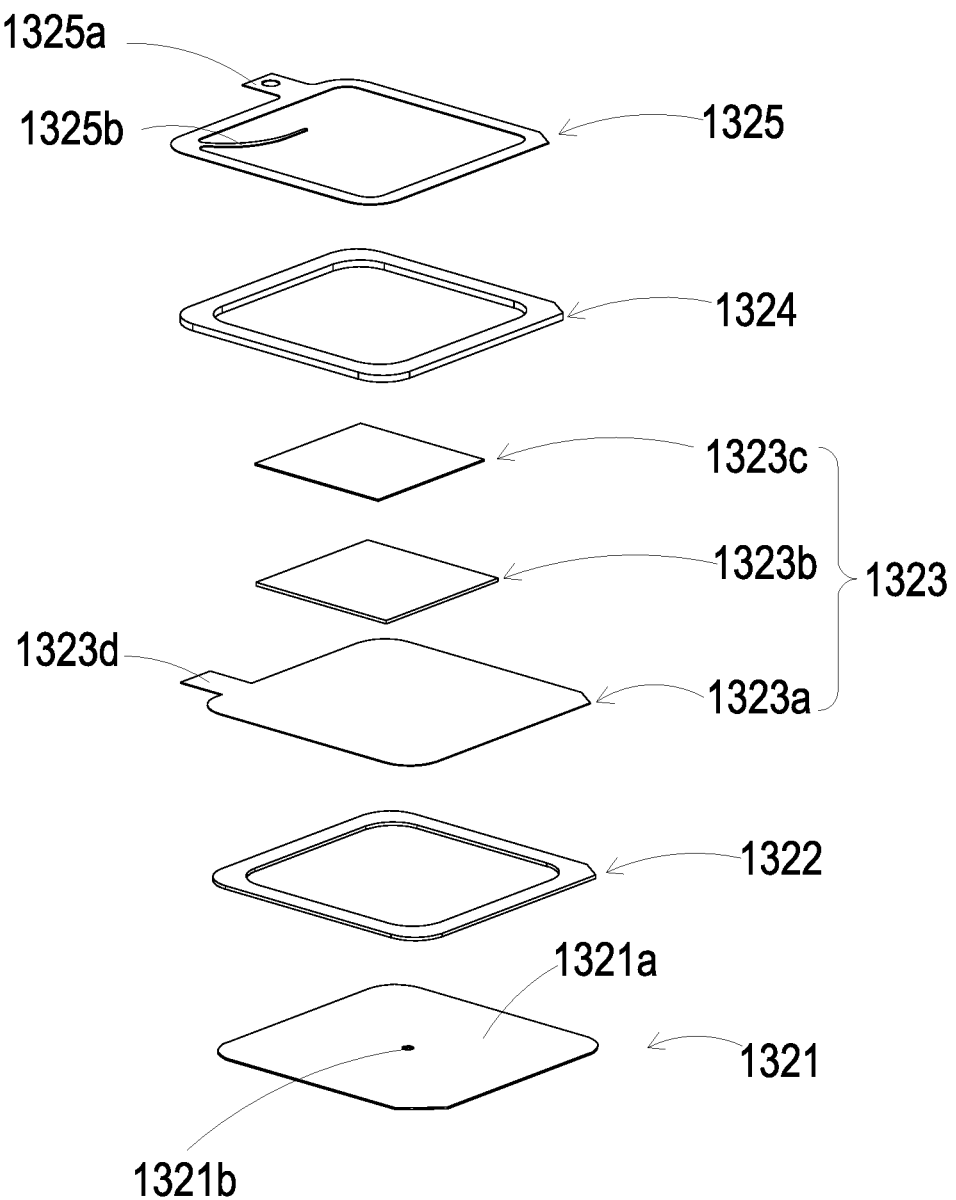
FIG. 6A is a schematic exploded view illustrating the piezoelectric actuator of the present disclosure.
Figure 6B:
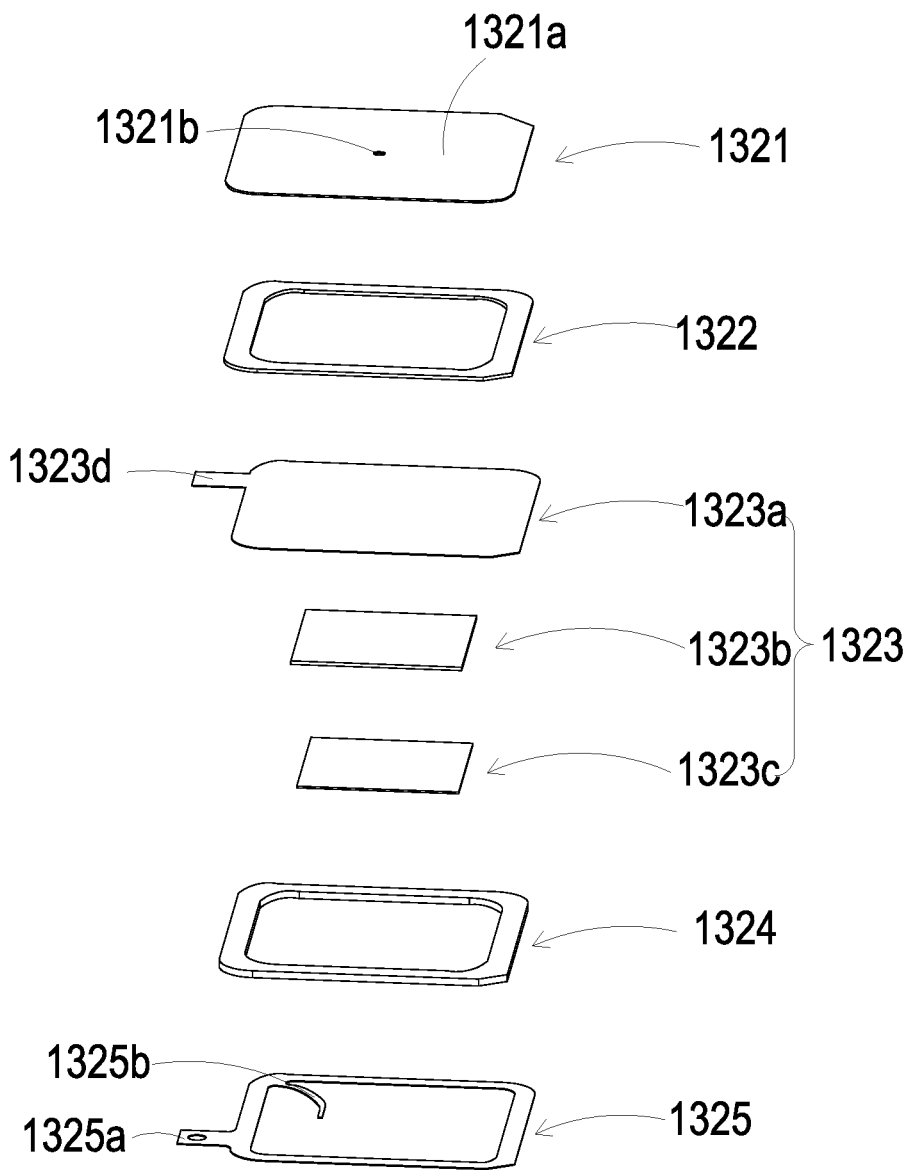
FIG. 6B is a schematic exploded view illustrating the piezoelectric actuator of the present disclosure and taken from another perspective angle.

Please refer to FIGS. 6A and 6B. In the embodiment, the piezoelectric actuator 132 includes a gas-injection plate 1321, a chamber frame 1322, an actuator element 1323, an insulation frame 1324 and a conductive frame 1325.

In the embodiment, the gas-injection plate 1321 is made by a flexible material and includes a suspension plate 1321a and a hollow aperture 1321b. The suspension plate 1321a is a sheet structure and permitted to undergo a bending deformation. Preferably but not exclusively, the shape and the size of the suspension plate 1321a are corresponding to an inner edge of the gas-guiding-component loading region 1315. The shape of the suspension plate 1321a is one selected from the group consisting of a square, a circle, an ellipse, a triangle and a polygon. The hollow aperture 1321b passes through a center of the suspension plate 1321a, so as to allow the gas to flow through.

In the embodiment, the chamber frame 1322 is stacked on the gas-injection plate 1321. In addition, the shape of the chamber frame 1322 is corresponding to the gas-injection plate 1321. The actuator element 1323 is stacked on the chamber frame 1322. A resonance chamber 1326 is collaboratively defined between the actuator element 1323, the chamber frame 1322 and the suspension plate 1321a. The insulation frame 1324 is stacked on the actuator element 1323 and the appearance of the insulation frame 1324 is similar to that of the chamber frame 1322. The conductive frame 1325 is stacked on the insulation frame 1324, and the appearance of the conductive frame 1325 is similar to that of the insulation frame 1324. In addition, the conductive frame 1325 includes a conducting pin 1325a and a conducting electrode 1325b. The conducting pin 1325a is extended outwardly from an outer edge of the conductive frame 1325, and the conducting electrode 1325b is extended inwardly from an inner edge of the conductive frame 1325. Moreover, the actuator element 1323 further includes a piezoelectric carrying plate 1323a, an adjusting resonance plate 1323b and a piezoelectric plate 1323c. The piezoelectric carrying plate 1323a is stacked on the chamber frame 1322. The adjusting resonance plate 1323b is stacked on the piezoelectric carrying plate 1323a. The piezoelectric plate 1323c is stacked on the adjusting resonance plate 1323b. The adjusting resonance plate 1323b and the piezoelectric plate 1323c are accommodated in the insulation frame 1324. The conducting electrode 1325b of the conductive frame 1325 is electrically connected to the piezoelectric plate 1323c. In the embodiment, the piezoelectric carrying plate 1323a and the adjusting resonance plate 1323b are made by a conductive material, but is not limit thereto. The piezoelectric carrying plate 1323a includes a piezoelectric pin 1323d. The piezoelectric pin 1323d and the conducting pin 1325a are electrically connected to a driving circuit (not shown) of the driving circuit board 133, so as to receive a driving signal, such as a driving frequency and a driving voltage. Therefore, a circuit is formed by the piezoelectric pin 1323d, the piezoelectric carrying plate 1323a, the adjusting resonance plate 1323b, the piezoelectric plate 1323c, the conducting electrode 1325b, the conductive frame 1325 and the conducting pin 1325a for transmitting the driving signal. Moreover, the insulation frame 1324 is insulated between the conductive frame 1325 and the actuator element 1323, so as to avoid the occurrence of a short circuit. Thereby, the driving signal is transmitted to the piezoelectric plate 1323c. After receiving the driving signal such as the driving frequency and the driving voltage, the piezoelectric plate 1323c deforms due to the piezoelectric effect, and the piezoelectric carrying plate 1323a and the adjusting resonance plate 1323b are further driven to generate the bending deformation in the reciprocating manner.

As described above, the adjusting resonance plate 1323b is located between the piezoelectric plate 1323c and the piezoelectric carrying plate 1323a and served as a buffer between the piezoelectric plate 1323c and the piezoelectric carrying plate 1323a. Thereby, the vibration frequency of the piezoelectric carrying plate 1323a is adjustable. Basically, the thickness of the adjusting resonance plate 1323b is greater than the thickness of the piezoelectric carrying plate 1323a, and the thickness of the adjusting resonance plate 1323b is adjustable, thereby adjusting the vibration frequency of the actuator element 1323.

Please refer to FIGS. 6A to 6C and FIG. 7A. In the embodiment, the gas-injection plate 1321, the chamber frame 1322, the actuator element 1323, the insulation frame 1324 and the conductive frame 1325 are stacked and positioned in the gas-guiding-component loading region 1315 sequentially, so that the piezoelectric actuator 132 is supported and positioned in the gas-guiding-component loading region 1315. The bottom of the gas-injection plate 1321 is fixed, supported and positioned on the four positioning protrusions 1315b of the gas-guiding-component loading region 1315, so that the suspension plate 1321a of the gas-injection plate 1321 and an inner edge 1315c of the gas-guiding-component loading region 1315 define a vacant space 1321c in the piezoelectric actuator 132 for the gas to flow through. Moreover, a flowing chamber 1327 is formed between the gas-injection plate 1321 and the bottom surface 1315d of the gas-guiding-component loading region 1315. The flowing chamber 1327 is in fluid communication with the resonance chamber 1326 between the actuator element 1323, the chamber frame 1322 and the suspension plate 1321a through the hollow aperture 1321b of the gas-injection plate 1321. By controlling the vibration frequency of the gas in the resonance chamber 1326 to be approached to the vibration frequency of the suspension plate 1321a, the Helmholtz resonance effect is generated between the resonance chamber 1326 and the suspension plate 1321a, and thereby improving the efficiency of gas transportation.

Figure 7A:
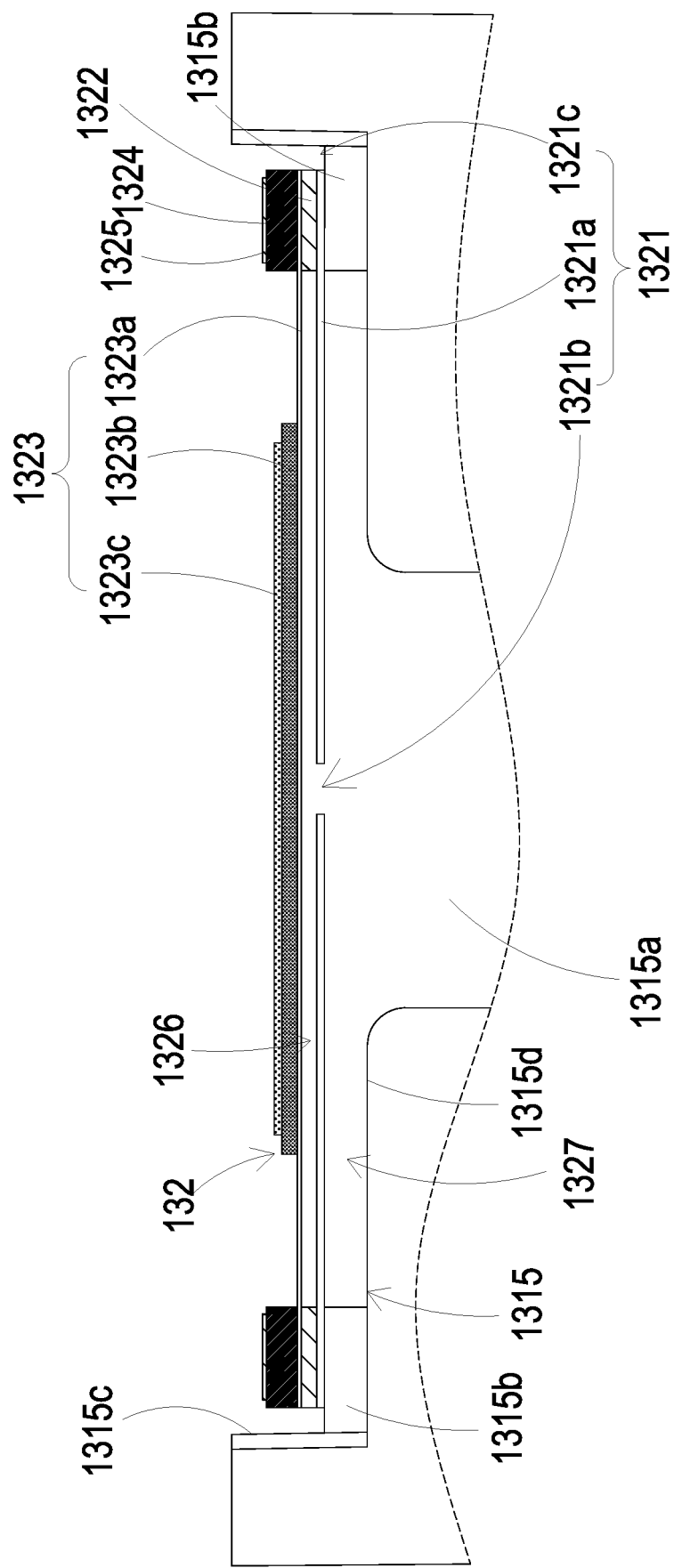
FIG. 7A is a schematic cross-sectional view illustrating the piezoelectric actuator accommodated in the gas-guiding-component loading region according to the present disclosure.
Figure 7B:
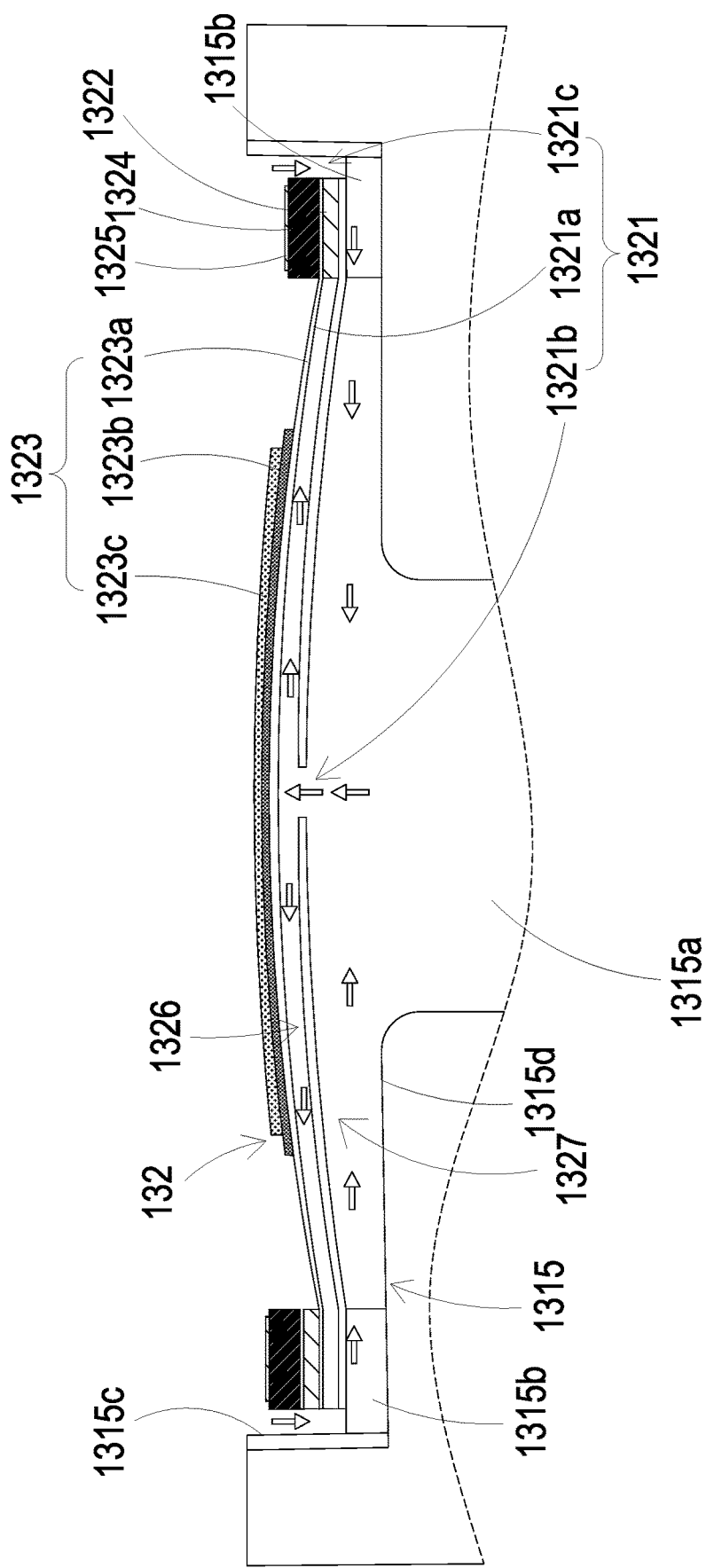
FIGS. 7B and 7C schematically illustrate the actions of the piezoelectric actuator of FIG. 7A.
Figure 7C:
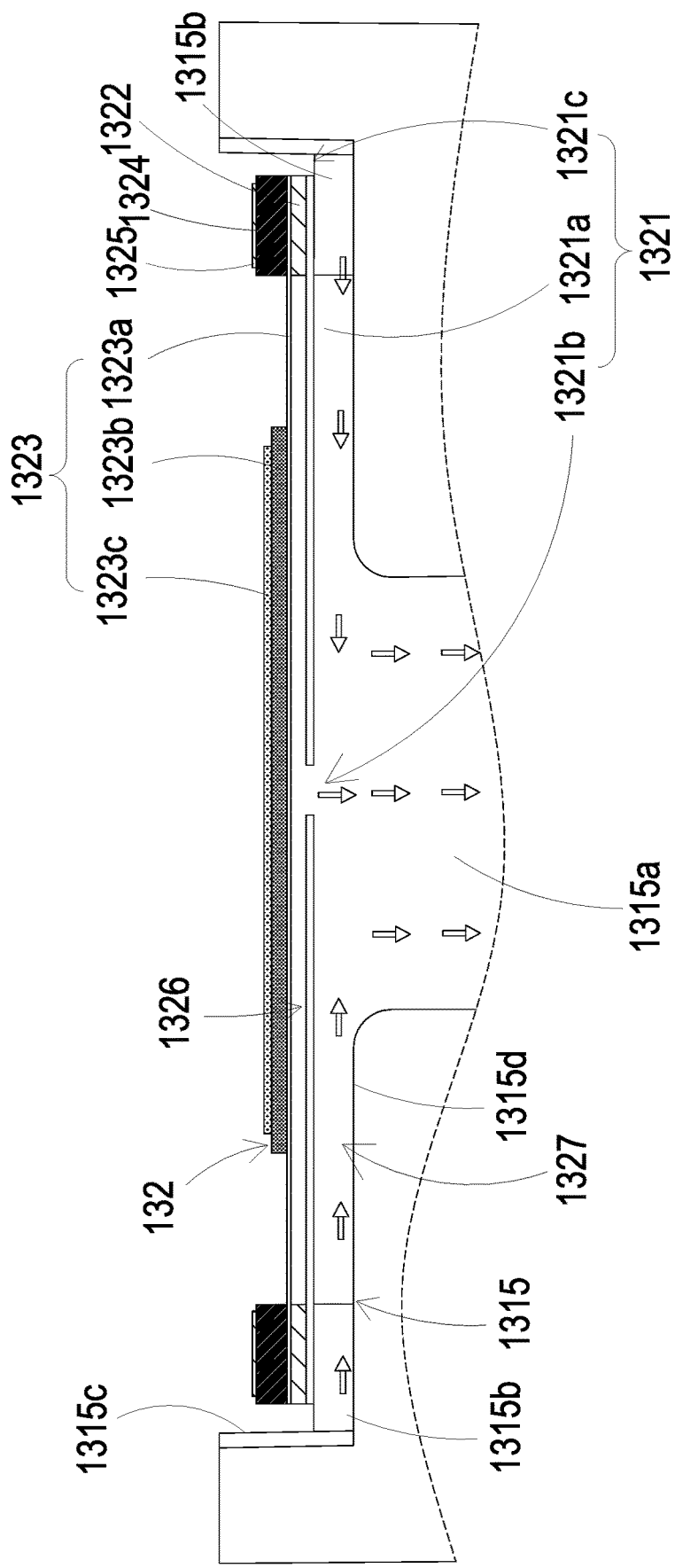

FIGS. 7B and 7C schematically illustrate the actions of the piezoelectric actuator of FIG. 7A. Please refer to FIG. 7B. When the piezoelectric plate 1323c is moved away from the bottom surface 1315d of the gas-guiding-component loading region 1315, the suspension plate 1321a of the gas-injection plate 1321 is driven to move away from the bottom surface 1315d of the gas-guiding-component loading region 1315 by the piezoelectric plate 1323c. As a result, the volume of the flowing chamber 1327 is expanded rapidly, the internal pressure in the flowing chamber 1327 is decreased and formed a negative pressure, and the gas outside the piezoelectric actuator 132 is inhaled through the vacant spaces 1321c and then entered the resonance chamber 1326 through the hollow aperture 1321b. Consequently, the pressure in the resonance chamber 1326 is increased and generated a pressure gradient. Further as shown in FIG. 7C, when the suspension plate 1321c of the gas-injection plate 1321 is driven by the piezoelectric plate 1323c to move towards the bottom surface 1315d of the gas-guiding-component loading region 1315, the gas in the resonance chamber 1326 is discharged out rapidly through the hollow aperture 1321b, and the gas in the flowing chamber 1327 is compressed. As a result, the converged gas is quickly and massively ejected out of the flowing chamber 1327 in a condition close to an ideal gas state of the Benulli's law, and transported to the ventilation hole 1315a of the gas-guiding-component loading region 1315. According to the principle of inertia, since the gas pressure inside the resonance chamber 1326 after exhausting is lower than the equilibrium gas pressure, the gas is introduced into the resonance chamber 1326 again. By repeating the above actions shown in FIG. 7B and FIG. 7C, the piezoelectric plate 1323c is driven to generate the bending deformation in a reciprocating manner. Moreover, the vibration frequency of the gas in the resonance chamber 1326 is controlled to be close to the vibration frequency of the piezoelectric plate 1323c, so as to generate the Helmholtz resonance effect to achieve the gas transportation at high speed and in large quantities.

Figure 8B:
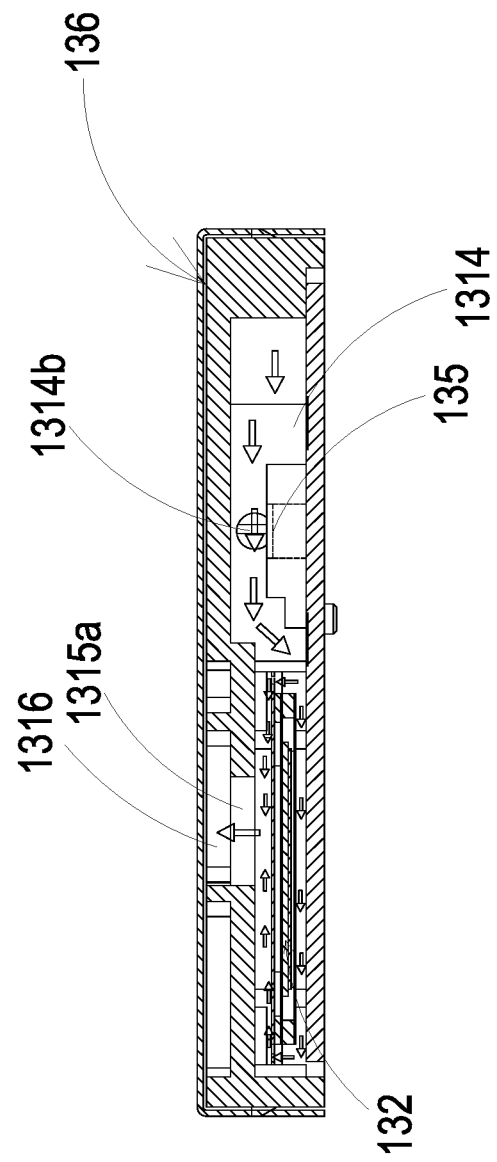
Figure 8C:
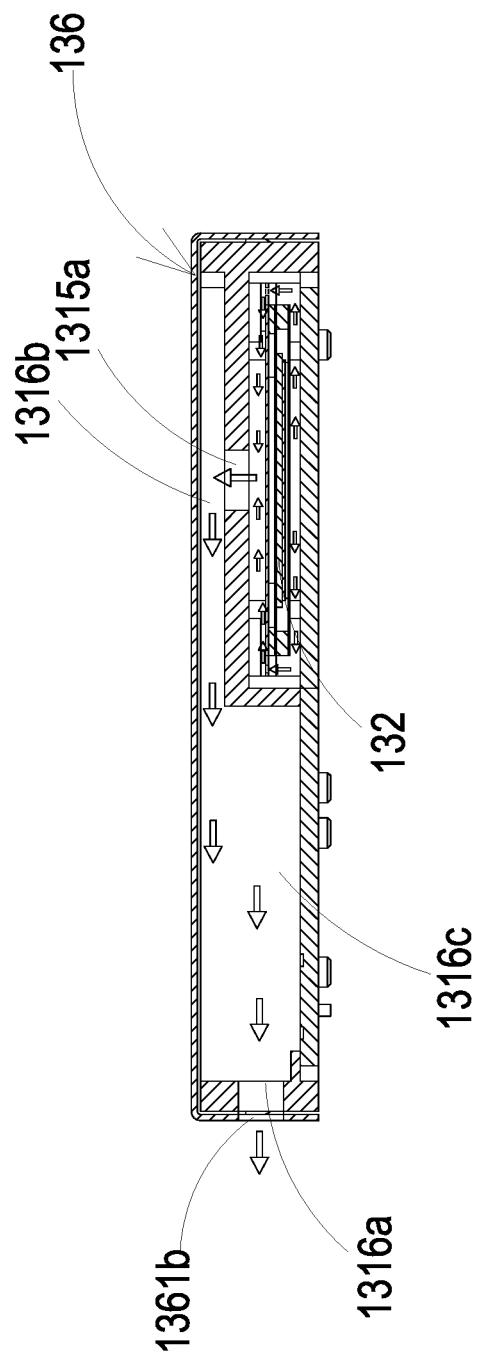

Please refer to FIGS. 8A to 8C. FIGS. 8A to 8C schematically illustrate gas flowing paths of the gas detection module. Firstly, as shown in FIG. 8A, the gas is inhaled through the inlet opening 1361a of the outer cover 136, flowed into the gas-inlet groove 1314 of the base 131 through the gas-inlet 1314a, and is transported to the position of the particulate sensor 135. Further as shown in FIG. 8B, the piezoelectric actuator 132 is enabled continuously to inhale the gas in the inlet path, and it facilitates the gas to be introduced rapidly, flowed stably, and passed above the particulate sensor 135. At this time, a projecting light beam emitted from the laser component 134 passes through the transparent window 1314b to irritate the suspended particles contained in the gas flowing above the particulate sensor 135 in the gas-inlet groove 1314. When the suspended particles contained in the gas are irradiated and generated scattered light spots, the scattered light spots could be received and calculated by the particulate sensor 135 for obtaining related information in regards to the sizes and the concentration of the suspended particles contained in the gas. Moreover, the gas above the particle sensor 135 is continuously driven and transported by the piezoelectric actuator 132, flowed into the ventilation hole 1315a of the gas-guiding-component loading region 1315, and transported to the first section 1316b of the gas-outlet groove 1316. As shown in FIG. 8C, after the gas flows into the first section 1316b of the gas-outlet groove 1316, the gas is continuously transported into the first section 1316b by the piezoelectric actuator 132, and the gas in the first section 1316b would be pushed to the second section 1316c. Finally, the gas is discharged out through the gas-outlet 1316a and the outlet opening 1361b.

Figure 9:
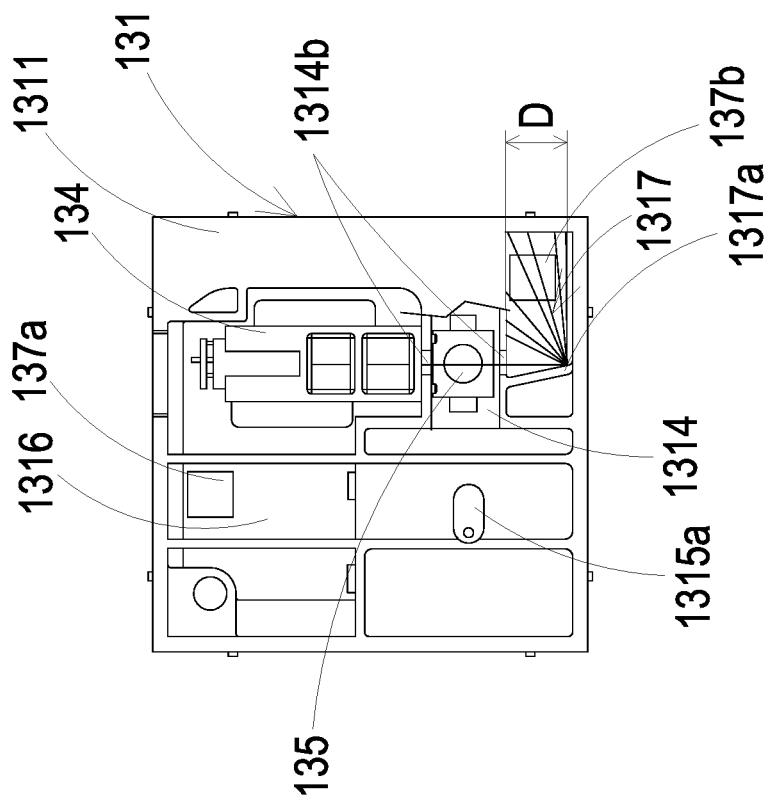
FIG. 9 schematically illustrates a light beam path emitted from the laser component of the gas detection module of the present disclosure.

As shown in FIG. 9, the base 131 further includes a light trapping region 1317. The light trapping region 1317 is hollowed out from the first surface 1311 to the second surface 1312 and spatially corresponds to the laser loading region 1313. In the embodiment, the light trapping region 1317 is corresponding to the transparent window 1314b so that the light beam emitted by the laser component 134 is projected into the light trapping region 1317. The light trapping region 1317 includes a light trapping structure 1317a having an oblique cone surface. The light trapping structure 1317a spatially corresponds to the light beam path emitted from the laser component 134. In addition, the projecting light beam emitted from the laser component 134 is reflected into the light trapping region 1317 by the oblique cone surface of the light trapping structure 1317a so as to prevent the projecting light beam from being reflected to the position of the particulate sensor 135. In the embodiment, a light trapping distance D is maintained between the transparent window 1314b and a position where the light trapping structure 1317a receives the projecting light beam. Preferably but not exclusively, the light trapping distance D is greater than 3 mm. When the light trapping distance D is less than 3 mm, the projecting light beam projected on the light trapping structure 1317a is easy to be reflected back to the position of the particulate sensor 135 directly due to excessive stray light generated after reflection, and it reduces detection accuracy and results in distortion thereof.

Please refer to FIG. 2C and FIG. 9. The gas detection module 13 of the present disclosure is not only utilized in detection of the suspended particles in the gas, but also further utilized in detection of the characteristics of the introduced gas. Preferably but not exclusively, the gas could be detected is at least one selected from the group consisting of formaldehyde, ammonia, carbon monoxide, carbon dioxide, oxygen, ozone and a combination thereof. In the embodiment, the gas detection module further includes a first volatile-organic-compound sensor 137a positioned and disposed on the driving circuit board 133, electrically connected to the driving circuit board 133, and accommodated in the gas-outlet groove 1316, so as to detect the gas flowing through the outlet path of the gas-outlet groove 1316. Thus, the concentration or the characteristics of volatile organic compounds contained in the gas in the outlet path is detected. Alternatively, in an embodiment, the gas detection module 13 further includes a second volatile-organic-compound sensor 137b positioned and disposed on the driving circuit board 133, and electrically connected to the driving circuit board 133. In the embodiment, the second volatile-organic-compound sensor 137b is accommodated in the light trapping region 1317. Thus, the concentration or the characteristics of volatile organic compounds contained in the gas flowing through the inlet path of the gas-inlet groove 1314 and transporting into the light trapping region 1317 through the transparent window 1314b could be detected.

Moreover, the transmission unit 122 is connected to the internet of things processing device 2 through a wire communication transmission or a wireless communication transmission. Preferably but not exclusively, the wire communication transmission is a USB transmission, and the wireless communication transmission is one selected from the group consisting of a Wi-Fi transmission, a Bluetooth transmission, a radio frequency identification transmission, and a near field communication (NFC) transmission.

In summary, the air detection system provided in the present disclosure combines a gas detection module with an intelligent device, such as an intelligent city, an intelligent building, an intelligent factory, a public air quality detector, an intelligent street lamp, a security surveillance camera, or a HVAC (heating, ventilation and air conditioner). The air detection system provided in the present disclosure can detect air in any area so as to obtain a gas information in real time and provide air quality information in any area to the user. When the gas exposure in the environment is detected to be harmful to the human health, the air detection system sounds an alert to the user in the environment and helps people to evacuate from the hazard environment immediately, so as to take preventive measures in real time to avoid the harm. The present invention therefore fulfills the industrial applicability requirement.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An air detection system, comprising:
   at least one intelligent device, comprising:
      at least one inlet;

at least one outlet;
a gas-flowing channel disposed between the at least one inlet and the at least one outlet;
a control module disposed in the intelligent device and comprising a processor and a transmission unit; and
a gas detection module disposed in the gas-flowing channel, electrically connected to the control module, and comprising a piezoelectric actuator, at least one sensor, a base and a laser component, wherein the piezoelectric actuator inhales gas outside the intelligent device into the gas-flowing channel through the at least one inlet and discharges the gas through the at least one outlet, wherein the at least one sensor detects the gas introduced to obtain a gas information and the gas information is transmitted to the control module, wherein the base comprises a gas-inlet groove, and the at least one sensor comprises a particulate sensor accommodated in the gas-inlet groove, wherein a light beam path emitted from the laser component extends in a direction perpendicular to the gas-inlet groove and the particulate sensor; and
an internet of things (IoT) processing device connected to the transmission unit of the at least one intelligent device for receiving the gas information transmitted from the at least one intelligent device.

2. The air detection system according to claim 1, wherein the at least one intelligent device is one selected from the group consisting of an intelligent city, an intelligent building, an intelligent factory, a public air quality detector, an intelligent street lamp, a security surveillance camera, and a HVAC and a combination thereof.

3. The air detection system according to claim 1, wherein the gas detection module comprises:
the base comprising:
a first surface;
a second surface opposite to the first surface;
a laser loading region hollowed out from the first surface to the second surface;
the gas-inlet groove recessed from the second surface and disposed adjacent to the laser loading region, wherein the gas-inlet groove comprises a gas-inlet and two lateral walls, the gas-inlet is in communication with an environment outside the base, and a transparent window is opened on the two lateral walls and is in communication with the laser loading region;
a gas-guiding-component loading region recessed from the second surface and in communication with the gas-inlet groove, wherein a ventilation hole penetrates a bottom surface of the gas-guiding-component loading region, and the gas-guiding-component loading region has four positioning protrusions disposed at four corners thereof; and
a gas-outlet groove recessed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;
a driving circuit board covering and attached to the second surface of the base;
the laser component positioned and disposed on the driving circuit board, electrically connected to the driving circuit board, and accommodated in the laser loading region, wherein the light beam path emitted from the laser component passes through the transparent window; and
an outer cover covering the first surface of the base and comprising a side plate, wherein the side plate has an inlet opening spatially corresponding to the gas-inlet and an outlet opening spatially corresponding to the gas-outlet, respectively,
wherein the piezoelectric actuator is accommodated in the gas-guiding-component loading region and fixed on the four positioning protrusions, wherein the particulate sensor is positioned and disposed on the driving circuit board, electrically connected to the driving circuit board, and disposed at a position where the gas-inlet groove intersects the light beam path of the laser component in the orthogonal direction, so that suspended particles passing through the gas-inlet groove and irradiated by a projecting light beam emitted from the laser component are detected, wherein the first surface of the base is covered with the outer cover, and the second surface of the base is covered with the driving circuit board, so that an inlet path is defined by the gas-inlet groove, and an outlet path is defined by the gas-outlet groove, so that the gas is inhaled from the environment outside base by the piezoelectric actuator, transported into the inlet path defined by the gas-inlet groove through the inlet opening, and passed through the particulate sensor to detect the concentration of the suspended particles contained in the gas, and the gas transported through the piezoelectric actuator is transported into the outlet path defined by the gas-outlet groove through the ventilation hole and then discharged through the outlet opening.

4. The air detection system according to claim 3, wherein the base comprises a light trapping region hollowed out from the first surface to the second surface and spatially corresponding to the laser loading region, wherein the light trapping region comprises a light trapping structure having an oblique cone surface and spatially corresponding to the light beam path.

5. The air detection system according to claim 4, wherein a light trapping distance is maintained between the transparent window and a position where the light trapping structure receives the projecting light beam.

6. The air detection system according to claim 5, wherein the light trapping distance is greater than 3 mm.

7. The air detection system according to claim 4, further comprising a first volatile-organic-compound sensor positioned and disposed on the driving circuit board, electrically connected to the driving circuit board, and accommodated in the gas-outlet groove, so as to detect the gas flowing through the outlet path of the gas-outlet groove.

8. The air detection system according to claim 7, further comprising a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

9. The air detection system according to claim 3, wherein the particulate sensor is a PM2.5 sensor.

10. The air detection system according to claim 3, wherein the piezoelectric actuator comprises:

a gas-injection plate comprising a suspension plate and a hollow aperture, wherein the suspension plate is permitted to undergo a bending deformation, and the hollow aperture is formed at a center of the suspension plate;

a chamber frame stacked on the suspension plate;

an actuator element stacked on the chamber frame for being driven in response to an applied voltage to undergo the bending deformation in a reciprocating manner;

an insulation frame stacked on the actuator element; and a conductive frame stacked on the insulation frame, wherein the gas-injection plate is fixed, supported and positioned on the four positioning protrusions of the gas-guiding-component loading region, and the gas-injection plate and an inner edge of the gas-guiding-component loading region define a vacant space for gas to flow through, and a flowing chamber is formed between the gas-injection plate and a bottom surface of the gas-guiding-component loading region, a resonance chamber is formed between the actuator element, the chamber frame and the suspension plate, wherein when the actuator element is enabled and drives the gas-injection plate to move in resonance state, the suspension plate of the gas-injection plate is driven to generate the bending deformation in a reciprocating manner, and the gas is inhaled through the vacant space, flowed into and discharged out of the flowing chamber, so as to achieve gas transportation.

11. The air detection system according to claim 10, wherein the actuator element comprises:

a piezoelectric carrying plate stacked on the chamber frame;

an adjusting resonance plate stacked on the piezoelectric carrying plate; and a piezoelectric plate stacked on the adjusting resonance plate, wherein the piezoelectric plate is configured to receive the applied voltage and drive the piezoelectric carrying plate and the adjusting resonance plate to generate the bending deformation in the reciprocating manner.

* * * * *